United States Patent [19]

White

[11] Patent Number: 4,554,154

[45] Date of Patent: Nov. 19, 1985

[54] DENTAL PRODUCT AND METHOD OF DENTAL TREATMENT

[76] Inventor: Maurice J. E. White, 87 Lewis Rd., Wantirna South 3152, Victoria, Australia

[21] Appl. No.: 588,920

[22] Filed: Mar. 12, 1984

[30] Foreign Application Priority Data

Mar. 15, 1983 [AU] Australia ............................. PF8450

[51] Int. Cl.⁴ .............................................. A61C 15/00
[52] U.S. Cl. ........................................ 424/16; 424/52; 424/151; 424/83; 132/89; 132/93; 426/6; 428/515; 433/216; 433/217.1
[58] Field of Search .................... 424/48, 16; 433/216, 433/217; 428/515; 426/6; 132/89, 93

[56] References Cited

U.S. PATENT DOCUMENTS

| | | | |
|---|---|---|---|
| 3,285,750 | 11/1966 | Ishida .................................. | 426/6 |
| 3,838,702 | 10/1974 | Standish et al. .................... | 132/89 |
| 4,098,406 | 7/1978 | Otten et al. ......................... | 428/515 |
| 4,121,006 | 10/1978 | Harada et al. ...................... | 428/515 |
| 4,275,119 | 6/1981 | Weiner ................................ | 428/515 |
| 4,352,822 | 10/1982 | Cherukuri et al. ................. | 426/6 |
| 4,387,108 | 6/1983 | Koch et al. ......................... | 426/6 |

FOREIGN PATENT DOCUMENTS

| | | | |
|---|---|---|---|
| 511285 | 8/1980 | Australia .............................. | 433/216 |
| 26252 | 4/1981 | European Pat. Off. ............. | 424/48 |
| 80440 | 6/1983 | European Pat. Off. ............. | 132/93 |
| 2330869 | 1/1975 | Fed. Rep. of Germany ... | 433/217.1 |
| 2848237 | 5/1980 | Fed. Rep. of Germany ... | 433/217.1 |
| 2059266 | 4/1981 | United Kingdom .................. | 132/93 |

OTHER PUBLICATIONS

Chemical Abstracts, vol. 80, 1974, Abstract 124773a.

*Primary Examiner*—Ronald W. Griffin
*Attorney, Agent, or Firm*—Larson and Taylor

[57] ABSTRACT

A dental product in the form of chewable plastics in the form of strip or foam, capsule or cloth. The plastics includes a biologically acceptable adhesive and being masticatable to provide dental care. The dental product may also carry remineralizing, immunological and antibacterial agents.

8 Claims, No Drawings

DENTAL PRODUCT AND METHOD OF DENTAL TREATMENT

This invention relates to a dental product and a method of dental treatment and particularly relates to a dental aid that is conveniently able to clean all tooth surfaces, particularly pits and fissures which are most susceptible to decay and cannot be cleaned by brushing or flossing. It helps control plaque and deliver optimum levels of dental agents like dietary fluoride at optimum topical concentration and apply a protective coating to teeth.

Dental disease is due to accumulation of bacterial plaque on tooth surfaces producing toxins that inflame gums and acids that decay teeth when sugars which increase plaque growth, are present.

Dental diseases are prevented by reducing attack by avoiding sugars and by mechanical, dietary, chemical and immunological plaque control and by increased resistance to attack. To prevent acid formation and attack it is necessary to remove plaque from all surfaces of teeth before eating, clean teeth after eating to avoid the early return of plaque; avoid sugars particularly between meals, treat the tooth surface to stop plaque reattachment, strengthen tooth surfaces or inactivate the bacteria in plaque. The toothbrush like dental floss and other common tooth care aids is often inconvenient to use after eating at times of attack and cannot clean between teeth or into grooves on chewing surfaces where most holes develop.

In my Australian Pat. No. 511,285, I disclose a dental product that comprises a chewable fin and stem composed of a plastic film and cellular foam of cell wall thickness 0.0125 mm to 0.03 mm thick, which is ideally proportioned to clean all tooth surfaces thoroughly without damaging the hard and soft tissues of the mouth. The fin passes through the contact points between adjacent pairs of teeth in close arrangement with proximal surfaces of the teeth; the stem cleans around gum margins and the whole is chewable to force saliva inside the grooves in chewing surfaces as well as controlling delivery of dental agents. The disclosure of my early patent is incorporated herein.

According to the present invention there is provided a dental product comprising a substrate carrying a biologically acceptable adhesive. The term "biologically acceptable" as used herein refers to a product or composition that can be introduced to the human digestive system orally and can be processed by the system for eventual discharge without reacting with or damaging the skin, saliva or organs of the body.

The substrate may be a strip of maleable plastic or aluminium that covers and adapts to the shape of tooth surfaces, a chewable plastics strip, plastics foam shape, chewing stick, capsule or cloth; an encapsulated cleaning stick or toothbrush bristle containing many fine parallel fibres so the bristle ends conform to the shape of tooth surface for better cleaning, or a fibre chewing gum.

The substrate may carry the biologically acceptable adhesive by impregnation, in a lamination, by coating adhesively or in the case of a capsule or lozenge by encapsulation.

The biologically acceptable adhesive preferably contains one or more agents considered advantageous in reducing tooth decay and improving tooth and gum care. Such agents should have remineralizing, immunelogical, enzyme, lysozym or anti-bacterial properties. Such a preferred material is sodium fluoride or sodium monofluorophosphate although any dental fluoride material may be used. The product is preferably arranged to control delivery of optimal dietary fluoride, (1 mg/day in non-fluoride areas or 0.1 mg/day in fluoride areas) at optimal topical concentration (5–1000 ppm) at tooth surfaces. The agents may also include suitable flavouring compounds and additives and suitable breath fresheners. However it is better to remove food from teeth immediately after eating before it breaks down to cause bad breath.

The biologically inert adhesive is preferably high molecular weight polyisobutylene in "chewy" or liquified form with suitable flavouring solvents. The adhesive enhances the ability to remove plaque, and can impart a glossy cosmetic skin when applied to the tooth surfaces which is moisture, acid and plaque resistant.

According to a further aspect of the present invention, there is provided a method of dental treatment comprising applying to the teeth a dental product of the kind described above. Preferably the application is by flossing between teeth, chewing the product, then rubbing the gum margins of tooth surfaces with the masticated fibres of product.

According to a further aspect of my invention there is provided a dental product comprising packaging material for edible products, said material comprising masticatable plastics.

The purpose of my invention is to make it convenient to control delivery of dietary or topical agents and or to remove plaque and food, sugars and acid from all tooth surfaces immediately after eating, particularly after eating sugary foods between meals when most attack usually occurs undisturbed e.g. when eating a candy bar. If the confection is partly wrapped in about 15 micron film like linear low density food grade polyethylene (LLDPE) this material can be used to floss between teeth, chewed to force saliva into grooves in chewing surfaces to dilute sugars and acids that may be present and remineralize damaged surfaces of initial lesions. The resulting masticated fibre can wipe plaque from gum margins under tongue or finger pressure in the same way as the stem of my previous invention or a specially prepared dental tape, but fluoride *should not* be included in the wrapping. In similar ways existing product packaging can be modified to give this facility for tooth care. For example perforating the top fold of a plastic sandwich bag 12 mm from the end so it is readily removed for tooth care after eating.

Packaging in rolls is more suitable for school or display use. Personal packs are best in booklet form while for handicapped people and young children foam plastic pieces are more suitable, particularly those described in the previous Australian Pat. No. 511,285.

Examples of the invention will now be described by way of example only.

EXAMPLE

A 552 mm wide coil of low density polyethylene film tubing 0.0127 mm is slit into 12 mm strips, coated on one side with fluoridated flavoured polyisobutylene (Mol. wt. about 50,000) and runs of 50 metres rolled onto 25 mm diameter cores. The fluoride may be either sprayed or blown onto the strips of polyethylene or applied as fluoridated adhesive by rollers. When strips about 10 cm long are wound off for use, the flavoured fluoride "gum" is laminated inside the plastics film. In use, fluoride is released slowly as the dental tape cleans between teeth like dental floss. The tape is then chewed to a pulp, forcing fluoride at controlled optimum concentration (5-1000 ppm) into pits and fissures where most holes develop. The saliva dilutes sugar concentration, inactivates and buffers acid production and remineralizates initial lesions especially with fluoride, so forming a less soluble fluorapatite or tougher tooth surface and may seal off pits and fissures. The fluoride and adhesive with the pulped fibres is then wiped on labial, buccal and lingual tooth surfaces under tongue or finger pressure. Some fluoride is swallowed but this is less than 0.1 mg which makes little difference to daily dietary intake. However in non-fluoride areas it is possible to lift this to optimal dietary fluoride intake of 1 mg/day.

Young children and handicapped people usually have a highly developed masticatory mechanism which is checked and improved in this way to better control the food bolus and reduce the risk of accidental swallowing or inhalation as well as help achieve correct jaw development. Although manual skills can be improved by flossing, chewing is much easier so foam plastic units are ideal for beginners and affords a high level of protection to grooves in chewing surfaces that develop up to 80% of cavities even with fluoridation and good brushing.

The system described above is particularly compact. One pocket sized roll of tooth cleaning film or dental tape is enough for every child in a school to clean its teeth. Larger rolls can be used to place a strip of dental tape in sweet or food wrappings on automatic packaging machines, in books or magazines for advertising or educational purposes. Preferably, small rolls or booklets of tape are used for every day personal manual operation or class tooth care after lunch at school. It is understood that the tape may be impregnated with suitable flavourings or mouth fresheners and may be multicoloured to further enhance the aesthetic appeal to children. By the use of the dental tape described above, all tooth surfaces can be simply, conveniently and effectively cleaned whilst delivering optimal dietary fluoride and other agents at optimal topical concentration. The film can also be packaged singly or in booklet form with or without the adhesive. Strips can also be part of the packaging or wrapping of food for catering facilities. For example sandwich bags can have one side perforated 12 mm for edge of fold in the bag. A strip could also be sealed under the flap. Other examples embraced carry the biologically inert adhesive in cellular foam shapes, sticks, cloth, fibres or cleaning bristles of fine fibres. Soft fine resilient fibres in any form that can transmit pressure to undulating tooth surfaces will effectively remove plaque. These fibres may be prefabricated as in a foam, in multi-fibre toothbrush bristles or in cloth. Fibres may also be made during use when a thin plastic film is corrugated during the cleaning operation between the teeth like dental floss or when chewed to a pulp thereby producing fine resilient fibres.

The adhesive has an affinity for plaque and so enhances plaque removal, it also adheres to tooth surfaces and so provides a protective barrier against plaque reattachment or acid attack. The adhesive can also have cosmetic benefits by producing a glossy appearance to the teeth and can protect fillings from moisture after placement. The adhesive may be coated on maleable strip like aluminium that may be closely adapted to tooth surfaces to hold thereon desired concentrations of dental agents such as fluoride, anti-bacterial chlorohexidine and immunological lysozym so they are not diluted or removed by saliva.

It is further understood that the biologically inert adhesive impregnated by a suitable dental agent such as fluoride may be used as the chewy centre in an artificial sweet made of chewable plastic foam in the form of a capsule or lozenge. Suitable flavouring may be added to improve the taste and consequent demand for the product. However fluoride would only be included for known controlled delivery.

Hitherto comprehensive preventive tooth care involved relatively uncontrolled and far from optimal use of the toothbrush, fluoride toothpaste, dental floss, dietary fluoride via fluoridation, fluoride tablet or other supplement; topical fluoride via gels, custom tray application, mouth rinses, anti-bacterial or anti-plaque preparations and pit and fissure sealants. This has often caused damage to hard and soft tissues in the oral cavity and overdose levels of fluoride have often been demonstrated. The functions of all these different products are now combined and controlled in one simple type of product in a number of convenient forms.

It is further understood that the various shapes of the dental fibre whether derived from a film, a fibre, a foam or a multi-fibre extrusion or from other existing products for convenience with or without dental agents are incorporated in this invention.

Having now described my invention, what I claim is:

1. A method of dental treatment comprising flossing between the teeth with a dental product that comprises chewable plastics tape carrying a biologically acceptable adhesive containing one or more of remineralizing, immunological and anti-bacterial agents, chewing the tape to allow the adhesive to control release into saliva of the agent or agents, and rubbing the gum margins of tooth surfaces with the masticated fibres of the tape, the chewing and rubbing steps causing adhesive to coat the teeth and gum margins to inhibit the attachment of plaque.

2. A dental product for carrying out the method of claim 1 comprising chewable plastics tape carrying a biological inert adhesive containing one or more of remineralizing, immunological and anti-bacterial agents.

3. A dental product according to claim 2 wherein the chewable plastics tape is polyethylene tape that carries the biologically acceptable adhesive by any one of the following means:
impregnation,
in a lamination,
in a coating, or
encapsulation.

4. The dental product according to claim 2 wherein the immunological agent is lysozym and the anti-bacterial agent is chlorohexidine.

5. The dental product according to claim 2 wherein the remineralizing agent is fluoride in the form of sodium fluoride or sodium monofluorophosphate.

6. The dental product according to claim 2 wherein the biologically acceptable adhesive is high molecular weight polyisobutylene.

7. A dental product for carrying out the method of claim 1 comprising polyethylene tape coated with high molecular weight polyisobutylene containing fluoride.

8. The dental product of claim 7 wherein the polyethylene tape is a tear off portion of packaging material for edible products.

* * * * *